(12) United States Patent
Hoofnagle et al.

(10) Patent No.: US 8,147,480 B2
(45) Date of Patent: Apr. 3, 2012

(54) CATHETER FOR REDUCED REFLUX IN TARGETED TISSUE DELIVERY OF A THERAPEUTIC AGENT

(75) Inventors: John R. Hoofnagle, Woodstock, CT (US); Schorn Greg, Milford, MA (US); Terri Kapur, Sharon, MA (US); Daniel Keeley, Boston, MA (US)

(73) Assignee: Codman & Shurtleff, Inc. MA (US)

( * ) Notice: Subject to any disclaimer, the term of this patent is extended or adjusted under 35 U.S.C. 154(b) by 112 days.

(21) Appl. No.: 12/157,070

(22) Filed: Jun. 7, 2008

(65) Prior Publication Data

US 2009/0088730 A1   Apr. 2, 2009

Related U.S. Application Data

(63) Continuation-in-part of application No. 11/904,724, filed on Sep. 28, 2007, now Pat. No. 7,766,875.

(51) Int. Cl.
  *A61M 25/00* (2006.01)
(52) U.S. Cl. ......................... 604/523; 604/524
(58) Field of Classification Search .................. 604/523, 604/524, 29, 500
  See application file for complete search history.

(56) References Cited

U.S. PATENT DOCUMENTS

| | | |
|---|---|---|
| 3,713,447 A | 1/1973 | Adair |
| 4,547,194 A | 10/1985 | Moorehead |
| 4,559,046 A | 12/1985 | Groshong et al. |
| 4,787,882 A | 11/1988 | Claren |
| 4,995,868 A | 2/1991 | Brazier |
| 5,053,004 A | 10/1991 | Markel et al. |
| 5,462,523 A | 10/1995 | Samson et al. |
| 5,643,226 A | 7/1997 | Cosgrove et al. |
| 5,693,030 A | 12/1997 | Lee et al. |
| 5,720,720 A | 2/1998 | Laske et al. |
| 5,749,826 A * | 5/1998 | Faulkner ................ 600/29 |
| 5,895,378 A | 4/1999 | Nita |
| 5,908,405 A * | 6/1999 | Imran et al. ............ 604/508 |
| 5,931,831 A | 8/1999 | Linder |
| 5,984,908 A | 11/1999 | Davis et al. |
| 5,993,473 A | 11/1999 | Chan et al. |
| 6,094,598 A | 7/2000 | Elsberry et al. |
| 6,110,155 A | 8/2000 | Baudino |
| 6,183,462 B1 | 2/2001 | Beals |
| 6,210,346 B1 | 4/2001 | Hall et al. |
| 6,358,229 B1 | 3/2002 | Tihon |
| 6,428,498 B2 | 8/2002 | Uflacker |
| 6,456,886 B1 | 9/2002 | Howard, III et al. |
| 6,497,699 B1 | 12/2002 | Ludvig et al. |

(Continued)

FOREIGN PATENT DOCUMENTS

WO   WO 01/28619   4/2001

(Continued)

*Primary Examiner* — Kevin C Sirmons
*Assistant Examiner* — Brandy C Scott
(74) *Attorney, Agent, or Firm* — Cheryl F. Cohen, LLC (57) ABSTRACT

A therapeutic agent delivery system that includes a catheter having a proximal end and an opposite distal end. The catheter has a body with a lumen defined therein. The body of the catheter includes a non-bulbous region having a substantially uniform outer diameter and a bulbous region made from an elastically deformable material. While in a first state the bulbous region has a maximum outer diameter greater than the substantially uniform outer diameter of the non-bulbous region; and while in a second state the maximum outer diameter of the bulbous region is reduced relative to that while in the first state.

19 Claims, 9 Drawing Sheets

U.S. PATENT DOCUMENTS

| | | |
|---|---|---|
| 6,524,296 B1 | 2/2003 | Beals |
| 6,602,241 B2 | 8/2003 | Makower et al. |
| 6,749,583 B2 * | 6/2004 | Briscoe et al. ............. 604/96.01 |
| 6,768,425 B2 | 7/2004 | Flaherty et al. |
| 6,951,555 B1 * | 10/2005 | Suresh et al. ................. 604/524 |
| 7,069,634 B1 | 7/2006 | Elsberry |
| 7,108,680 B2 | 9/2006 | Rohr et al. |
| 7,335,187 B2 | 2/2008 | Altman |
| 2001/0021840 A1 | 9/2001 | Suresh et al. |
| 2001/0025169 A1 | 9/2001 | Kaneshige |
| 2002/0177866 A1 * | 11/2002 | Weikel et al. ................. 606/192 |
| 2005/0154297 A1 | 7/2005 | Gill |
| 2006/0094983 A1 | 5/2006 | Burbank et al. |
| 2006/0135945 A1 | 6/2006 | Bankiewicz et al. |
| 2007/0078386 A1 | 4/2007 | Salazar |
| 2007/0088295 A1 | 4/2007 | Bankiewicz |
| 2007/0112302 A1 | 5/2007 | Yu |

FOREIGN PATENT DOCUMENTS

| | | |
|---|---|---|
| WO | WO 02/00286 | 1/2002 |

* cited by examiner

CATHETER FOR REDUCED REFLUX IN TARGETED TISSUE DELIVERY OF A THERAPEUTIC AGENT

CROSS-REFERENCE TO RELATED APPLICATIONS

This application is a continuation-in-part of prior application Ser. No. 11/904,724, filed Sep. 28, 2007, which is herein incorporated by reference in its entirety.

BACKGROUND OF THE INVENTION

1. Field of the Invention

The present invention is directed to a catheter for drug delivery and, in particular, to a catheter for the delivery of a therapeutic agent into body tissue while reducing unwanted reflux.

2. Description of Related Art

Fluids or therapeutic agents may be delivered into various parts of the body that already contain a fluid or liquid such as epidurally or intrathecally into the spinal space. The delivery of a therapeutic agent into a fluid or liquid does not produce as much resistance or pressure as when dispensing directly into tissue. The fluid being dispensed from the catheter attempts to find the path of least pressure or resistance. In the case of tissue as the target of injection this path of least resistance or pressure often times causes the therapeutic agent to disadvantageously travel back up the catheter track defined as the space between the targeted tissue and outer surface of the catheter, otherwise referred to as reflux, back flow or leakage. Such back flow may result in catheter contamination or exposure of a larger area of the tissue to the therapeutic agent.

Convection enhanced delivery is the injection under positive pressure of fluid containing a therapeutic agent. This technology allows focused delivery of a therapeutic agent to a specific targeted area. Direct delivery is advantageous in that it reduces, if not eliminates, side effect complications that would otherwise arise from the delivery of a therapeutic agent systemically. Another advantage is that convection enhanced delivery can increase the activity of the drug and deliver therapeutic concentrations not possible using conventional means. Therapeutic agents previously unable to reach a targeted tissue through oral delivery may now be reconsidered for direct delivery.

In brain tissue, drug formulations are difficult to develop due to the blood-brain barrier transport properties. Typically, molecules enter the cerebral spinal fluid or brain tissue in three ways: (i) by diffusion of lipid-soluble substances, (ii) by facilitative and energy-dependent receptor-mediated transport of specific water-soluble substances, and (iii) by ion channels. Protein based drugs do not typically fall into any of these three categories, and thus are usually not amenable to oral or intravenous delivery.

Recent study has focused on the direct infusion of proteins in the brain as a possible treatment of Parkinson's disease. In particular, the treatment of Parkinson's disease has recently concentrated on the delivery of the therapeutic agent directly into the grey matter brain tissue such as in the putamen. Conventional catheters permit backflow and reflux back up the catheter track that produces undesirable side effects if used to deliver proteins to the putamen.

U.S. Patent Publication No. 2007/0088295 discloses a step-design cannula and delivery system for chronic delivery of therapeutic substances into the brain using convention-enhanced delivery of therapeutic substances and which effectively prevents reflux in vivo and maximizes distribution into the brain. A delivery sheath is used for positioning the infusion cannula in the brain. The proximal end of the delivery sheath functions as the most external segment of the step-design of the infusion cannula, thereby increasing the overall number of steps in the step-design. Once the delivery sheath and cannula are placed at the proper depth, the assembly is fixed in position, for example, using an o-ring shaped holding bracket through which a bone screw is inserted to rigidly attach the holding bracket to the skull. After the assembly is positioned, only the upper portion of the delivery sheath is removed by cutting the sheath just above the points where the infusion cannula bends over leaving in place that portion of the delivery sheath implanted in the body. The system in accordance with the published patent application employs a delivery sheath as a guide because the central lumen is populated from the source to the distal tip with an infusion tube and thus a stylet cannot be directly inserted into the central lumen. The use of a delivery sheath while positioning the cannula in such a manner and leaving it implanted thereafter is disadvantageous in that it provides an allowance or opening between the proximal end of the delivery sheath and the distal catheter that is prone to reflux and back flow of the therapeutic substance thereby defeating the underlying purpose of the device. In addition, the published patented application catheter has a single exit port through the distal end of the catheter.

It is therefore desirable to develop an improved catheter design for delivery of a therapeutic agent directly into tissue that reduces or prevents reflux and back flow while eliminating the need for a guide or delivery sheath during positioning. Furthermore, an improved catheter is needed with an adjustable flow rate via multiple output ports.

SUMMARY OF THE INVENTION

An aspect of the present invention is directed to a therapeutic agent delivery system that includes a catheter having a proximal end and an opposite distal end. The catheter has a body with a lumen defined therein. The body of the catheter includes a non-bulbous region having a substantially uniform outer diameter and a bulbous region made from an elastically deformable material. While in a first state the bulbous region has a maximum outer diameter greater than the substantially uniform outer diameter of the non-bulbous region; and while in a second state the maximum outer diameter of the bulbous region is reduced relative to that while in the first state. The maximum outer diameter of the bulbous region while in the second state is substantially equal to the substantially uniform outer diameter of the non-bulbous region. In a first embodiment of the present invention, the first state is a non-stressed state and the second state is a stressed state. An alternative embodiment is also presented in which the first state is a stressed state and the second state is a non-stressed state.

Another aspect of the present invention relates to a method for using the therapeutic agent delivery system described in the preceding paragraph. The delivery system includes a catheter having a proximal end and an opposite distal end. In addition, the catheter has a body with a lumen defined therein. The body of the catheter includes a non-bulbous region having a substantially uniform outer diameter and a bulbous region made from an elastically deformable material. Initially, a stylet is inserted into the lumen starting at the proximal end of the catheter and extending through at least the bulbous region. The assembled stylet and catheter is implanted in a patient at a targeted site while the bulbous region is in a first state in which the maximum outer diameter of the bulbous region is substantially equal to the substantially uniform outer diameter of the non-bulbous region. After the catheter has been properly positioned, the assembled stylet is removed from the catheter while the bulbous region of the catheter is maintained in a second state in which the maximum outer diameter of the bulbous region is greater than in the first state so as to reduce back flow.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

FIGS. 1-4 show a step catheter 100 in accordance with the present invention for delivery of a therapeutic agent, medicine, drug or other fluid directly to a targeted site such as a targeted tissue. The specific geometry or design of the catheter reduces or substantially prevents reflux, leakage and back flow while eliminating the need for a guide or delivery sheath during insertion and positioning.

Figure 1:
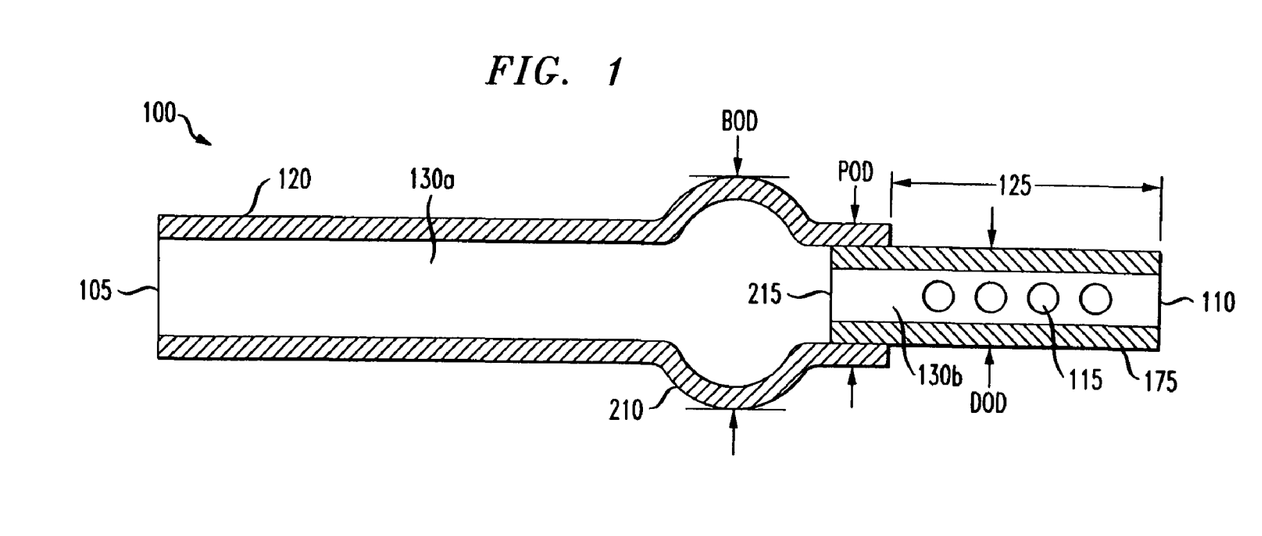
FIG. 1 represents a cross-sectional view of an exemplary step catheter in accordance with the present invention in a relaxed or non-stressed state with an enlarged bulbous region having a maximum outer diameter greater than that of a non-bulbous region having a substantially uniform outer diameter.

A first embodiment of the present invention is shown in FIGS. 1-7. Referring to FIG. 1, step catheter 100 has a proximal end or tip 105 and an opposite open distal end or tip 110. The distal end or tip 110 despite being shown open, may alternatively be closed or sealed. Step catheter 100 is formed by a proximal section 120 closest to the proximal end 105 coupled coaxially to a distal section 175 closest to the distal end 110. Each of the proximal and distal sections has a lumen 130a, 130b, respectively defined therein that together define a passageway from the proximal end 105 to the distal end 110 of the step catheter 100. The outer diameter (DOD) of the distal section 175 is smaller than the inner diameter of the lumen 130a of the proximal section 120 so that a portion of the proximal end of the distal section 175 may be telescopically received in the lumen 130a.

Proximal section 120 is preferably formed of an elastically deformable material (e.g., silicone or polyurethane) whereas distal section 175 is preferably formed of a substantially rigid material such as stainless steel, titanium, polyetherimide (PEI) or polyetheretherketone (PEEK). In a preferred embodiment, the length 125 of that portion of the distal section 175 which extends beyond the proximal section 120 is between approximately 1.0 cm to approximately 4.0 cm when used to deliver a therapeutic agent to the putamen. It is contemplated and within the intended scope of the present invention to vary this length, as desired, depending on the size and depth of the targeted tissue into which the catheter is to be inserted.

As previously mentioned, proximal section 120 is made of an elastically deformable material. Proximal section 120 of the catheter includes a bulbous region 210 proximate the distal section 175. Bulbous region 210 is made from a deformable material having an elastic shape memory. The bulbous region 210 may, but need not necessarily, be made using the same material as that forming the remaining portion of the proximal section 120. While in a relaxed or non-tensioned state, bulbous region 210 has an enlarged outer diameter (BOD) relative to a non-bulbous region of the proximal section 120 having a substantially uniform outer diameter (POD). This enlarged diameter (BOD) of bulbous region 210 relative to the otherwise substantially uniform outer diameter (POD) of the non-bulbous region of the proximal section 120 creates a barrier that substantially prevents or reduces reflux of infusate along the catheter track. Preferably, the maximum outer diameter (BOD) of the bulbous region 210 is approximately 1.7 mm, while the substantially uniform outer diameter (POD) of the non-bulbous region of proximal section 120 is approximately 1.4 mm.

The invention has been shown and described as having a single bulbous region 210, however, it is contemplated and within the intended scope of the present invention for the proximal section 120 to include more than one bulbous region, as desired. Bulbous region 210 may be fabricated directly into the material by insert molding. Alternatively, the bulbous region 210 may be formed by a member such as a shape memory alloy that is either deployed or located within the wall of the proximal section 120. As previously noted, the material used to form the bulbous region 210 may, but need not necessarily, be the same as that used for the non-bulbous region of the proximal section 120. The contour or cross-sectional shape of the bulbous region 210 need not be limited by that shown and described, instead any desired shape may be selected so long as: (i) when in a relaxed or non-stressed state the maximum outer diameter of the bulbous region is greater than that of the substantially uniform outer diameter of the non-bulbous region of the proximal section so that the outer diameter over the entire proximal section is non-uniform; and (ii) when in a stretched or stressed state the maximum outer diameter of the bulbous region is reduced relative to when in a relaxed or non-stressed state and, preferably, the maximum outer diameter over the entire proximal section is substantially uniform when the bulbous region is in a stretched or stressed state.

Step catheter 100 may be designed to have any number of one or more outlet ports disposed, as desired. By way of illustrative example, the distal end 110 of the step catheter 100 shown in FIGS. 1-4 is open and any number of one or more ports or openings 115, preferably between approximately 2 and approximately 50 openings, are defined radially therethrough the outer perimeter in the distal section 175. Each port or opening 115 may be any diameter, as desired. In a preferred embodiment, the diameter of each opening 115 is in the range between approximately 0.01 mm and approximately 4 mm. It is noted that the openings 115 shown in FIG. 1 are all substantially equal in diameter, however, the diameter of all of the openings need not be uniform. Furthermore, in the illustrative example shown in FIG. 1 the openings 115 are arranged or disposed substantially symmetrically about the outer perimeter of the distal section 175 of the catheter to permit substantially uniform delivery of the therapeutic agent in all directions. Alternatively, the arrangement or positioning of the openings 115 defined in the outer perimeter of the distal section 175 of the catheter may be asymmetric or altered in any desired configuration. In a preferred embodiment, optimal delivery is achieved when factors such as the number of openings or ports 115, and the diameter size and arrangement of such openings are selected so that the flux of all ports or openings 115 is maintained preferably between approximately 0.500 (μl/min)/mm$^2$ and approximately 1.000 (μl/min)/mm$^2$.

Figure 2:
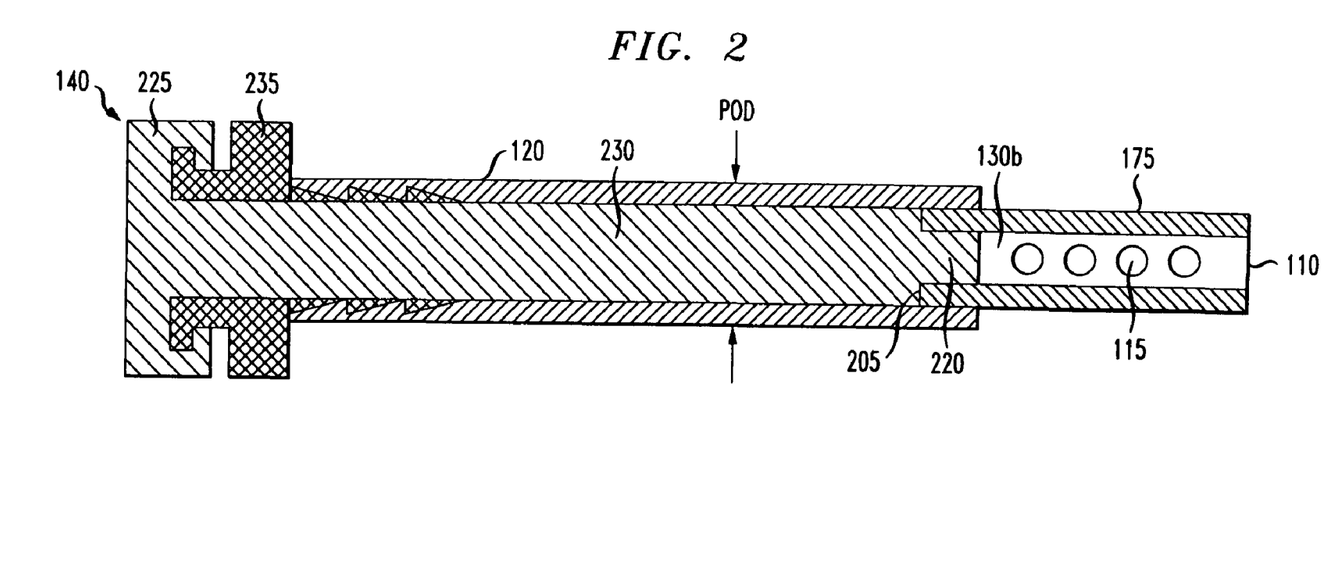
FIG. 2 depicts a cross-sectional view of the step catheter of FIG. 1 and assembled pre-loaded stylet locked therein using a barb connector with the bulbous region of the catheter in a stretched or stressed state having a reduced maximum outer diameter relative to that while in a relaxed or non-stressed state.

Prior to positioning the catheter at the targeted site, a stylet 140 is inserted through the lumen 130a of the proximal section 120 and into at least a portion of lumen 130b of the distal section 175 to stiffen the catheter in order to maintain trajectory during stereotaxy. To allow for insertion, a portion of the body 230 of the stylet 140 to be received in the lumen 130a of the proximal section 120 of the catheter has an outer diameter that is less than the inner diameter of the lumen 130a. When using a conventional stylet the body 230 of which has an outer diameter of approximately 0.45 mm, the lumen 130a has an inner diameter preferably of approximately 0.6 mm. FIG. 2 shows the step catheter 100 of FIG. 1, releasable connector 235 and interlocking stylet 140 assembled together. Stylet 140 includes a hub 225, a body 230, a shoulder 205 and an arm 220. The body 230 of stylet 140 is inserted through the lumen 130a until its shoulder 205 contacts the proximal end 215 of distal section 175. An axial force is applied to the stylet 140 relative to the catheter 100 causing the elastically deformable bulbous region 210 to be axially stretched until the proximal end 105 of the catheter 100 is able to be releasably locked or secured to the stylet hub 225 by either a friction fitting barb connector 235 (as shown in FIG. 2) or other releasable connector. When shoulder 205 is in contact with the proximal end 215 of distal section 175, arm 220 of stylet 140 extends at least partially into the portion of the lumen 130b disposed in distal section 175 to provide the necessary rigidity or strengthening over the entire length of the step catheter 100 during insertion so that it may be properly positioned proximate the targeted site. Preferably, arm 220 extends at least to the distal end of proximal section 120. It is contemplated and within the intended scope of the present invention for the distal tip of stylet 140 to extend substantially to the distal end or tip 110 of the catheter 100.

While in a stretched or tensioned state, as shown in FIG. 2, the enlarged outer diameter (BOD) of the bulbous region 210 is substantially reduced relative to that while in a relaxed or non-stressed state, which is desirable during catheter insertion to the targeted site. Preferably, if sufficient axial force is applied during the stretched or stressed state, the entire proximal section 120 will have a substantially uniform outer diameter (POD), as shown in FIG. 2.

Figure 3:
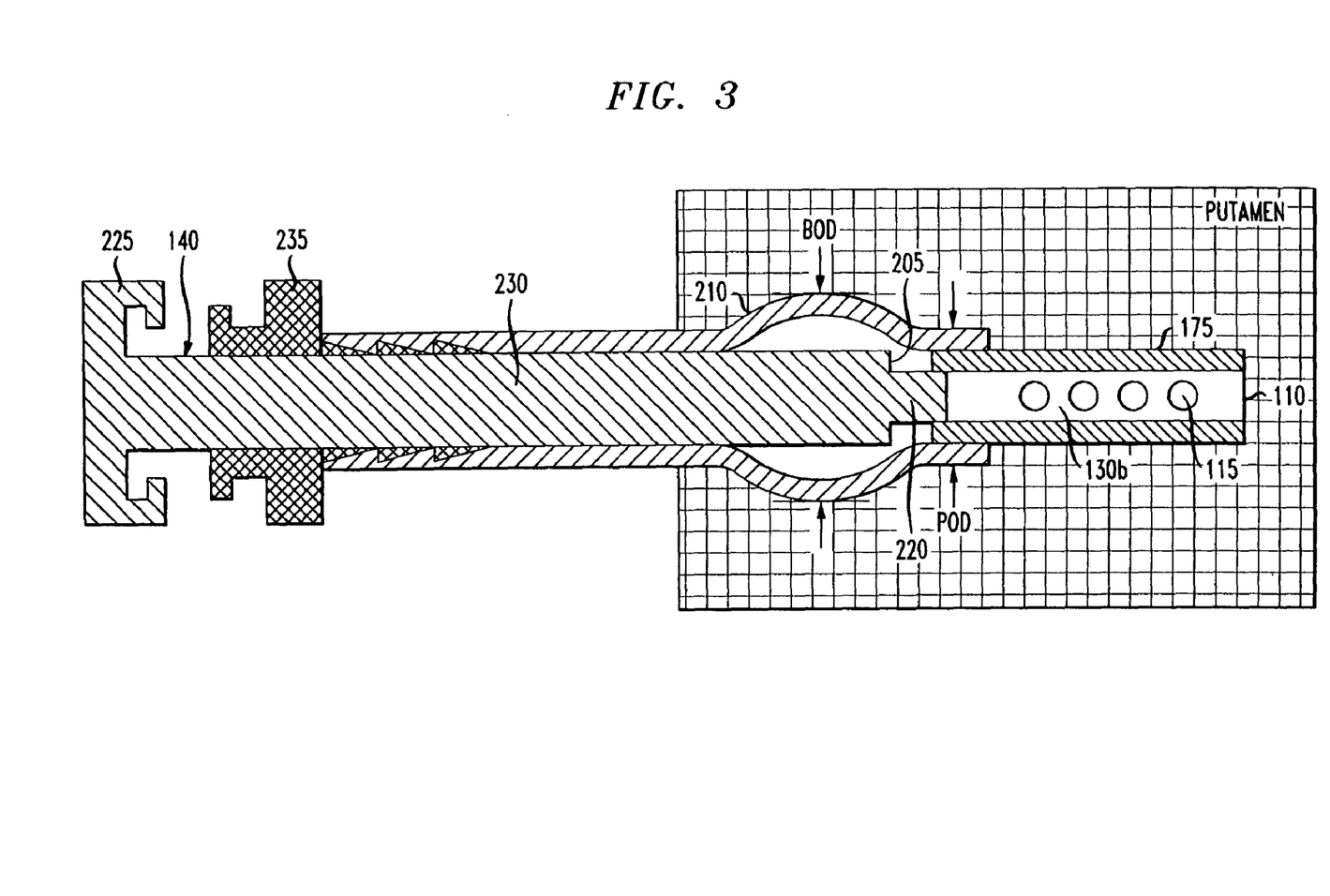
FIG. 3 depicts a cross-sectional view of the step catheter of FIG. 1 after it has been implanted at a targeted site with the stylet thereafter unlocked from the barb connector and the bulbous region of the catheter returned to its relaxed or non-stressed state in which its maximum outer diameter is greater than that of the non-bulbous region.
Figure 4:
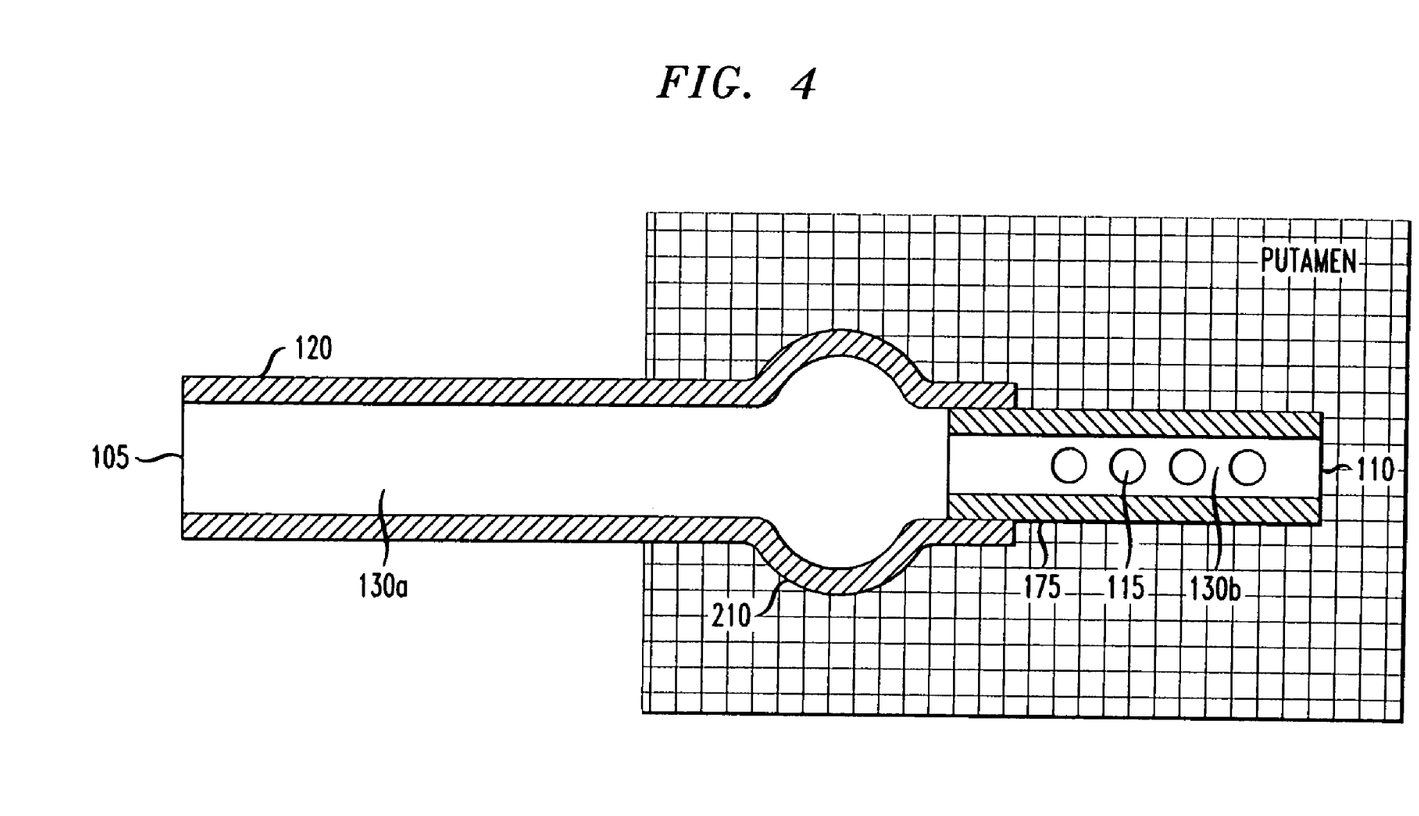
FIG. 4 shows a cross-sectional view of the step catheter of FIG. 1 positioned at the targeted site with the bulbous region in a relaxed or non-stressed state and the stylet and barb connector removed completely from the catheter.

Once the distal end 110 of the step catheter 100 has been properly positioned at the targeted site, the hub 225 of the stylet 140 is unlocked, unsecured or disengaged from the connector 235. The bulbous region 210 of the proximal section 120 is then allowed to retract axially and return to its relaxed or non-stressed state while the distal end 110 of the catheter remains substantially properly positioned at the targeted site, as shown in FIG. 3. As the bulbous region 210 of the proximal section of the catheter retracts axially, its maximum outer diameter (BOD) returns to its relaxed enlarged state applying outward radial pressure against the surrounding tissue circumferentially about the catheter creating a barrier that substantially prevents or reduces reflux of infusate along the catheter track. As illustrated in FIG. 4, once stylet 140 and connector 235 are removed, catheter 100 remains in place with its proximal end 105 attachable to a pump catheter (not shown), which is tunneled subcutaneously to the implanted pump. The infusate passes through lumens 130a, 130b and is dispensed out from the outlet ports 115 and open end of the catheter to the targeted tissue.

Figure 14:
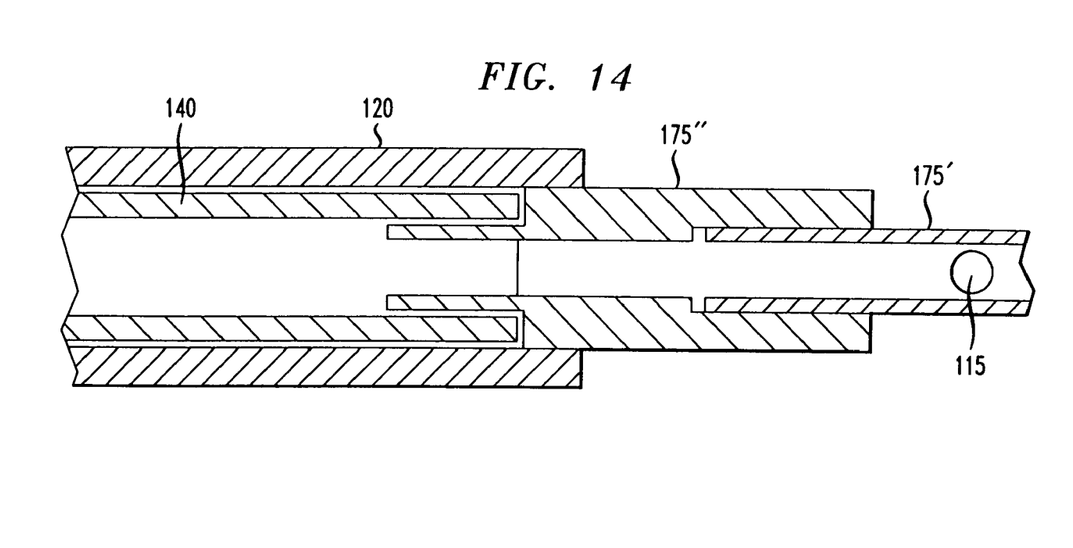
FIG. 14 represents a partial cross-sectional view of the step catheter and assembled pre-loaded stylet in accordance with an alternative embodiment interlocking configuration.

The embodiment shown and described in FIGS. 1-4 depicts a step catheter having a distal section 175 with a single step. Distal section 175 may be designed to include more than one step. FIG. 14 depicts a partial cross-sectional view of an alternative embodiment of the interlocking between a step catheter and stylet 140 assembled therein. The step catheter has a proximal section 120 and a distal section 175 comprising two stepped distal subsections 175', 175". In this alternative interlocking configuration, stylet 140 is received in a recess formed between the proximal section 120 and the distal subsection 175". Stylet 140 extends at least partially into the distal section 175 thereby providing rigidity or strengthening over the entire length of the step catheter during insertion so that it may be properly positioned proximate the targeted site.

Figure 5:
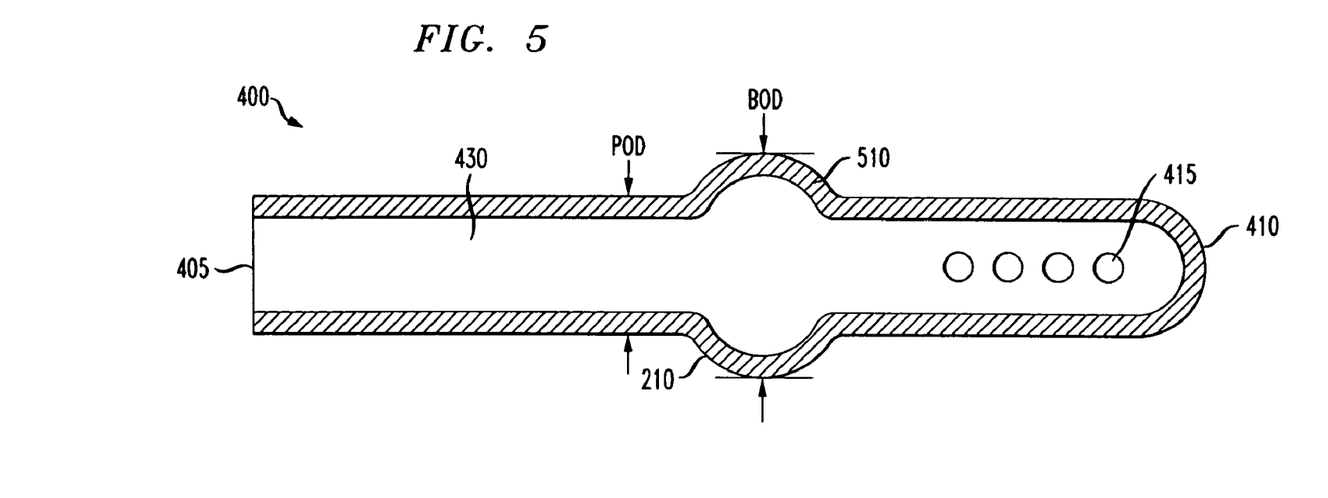
FIG. 5 depicts a cross-sectional view of a straight catheter with the bulbous region of the catheter in a relaxed or non-stressed state so that it has a maximum outer diameter greater than that of the non-bulbous region having a substantially uniform outer diameter.
Figure 6:
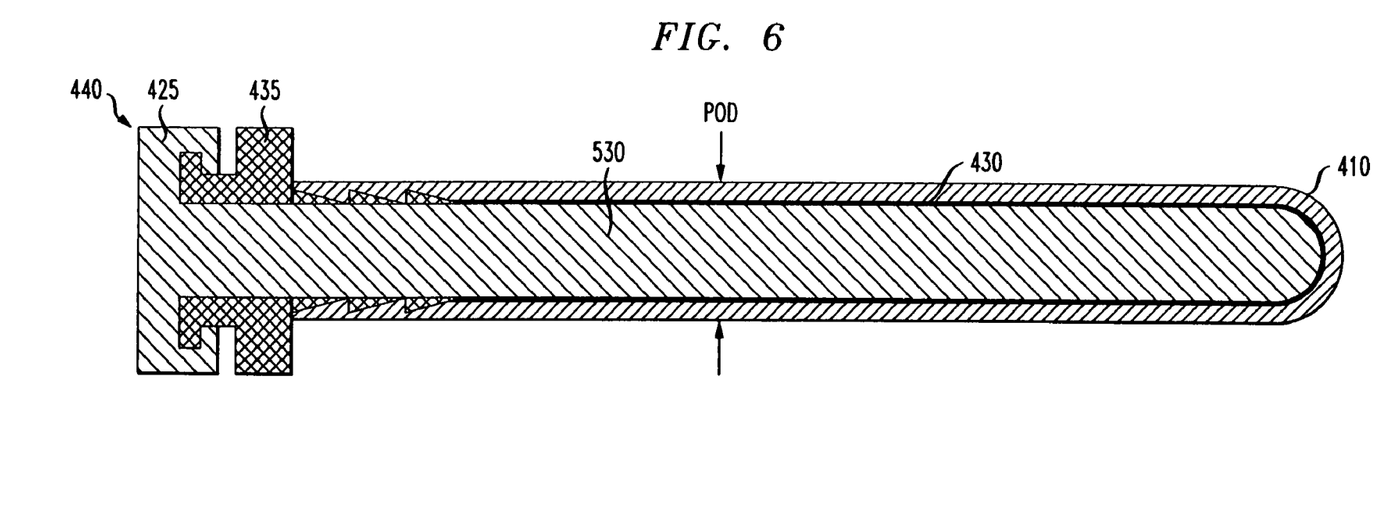
FIG. 6 represents a cross-sectional view of the straight catheter of FIG. 5 and assembled pre-loaded stylet locked therein using a barb connector with the bulbous region of the catheter in a stretched or stressed state having a reduced maximum outer diameter relative to that while in a relaxed or non-stressed state.
Figure 7:
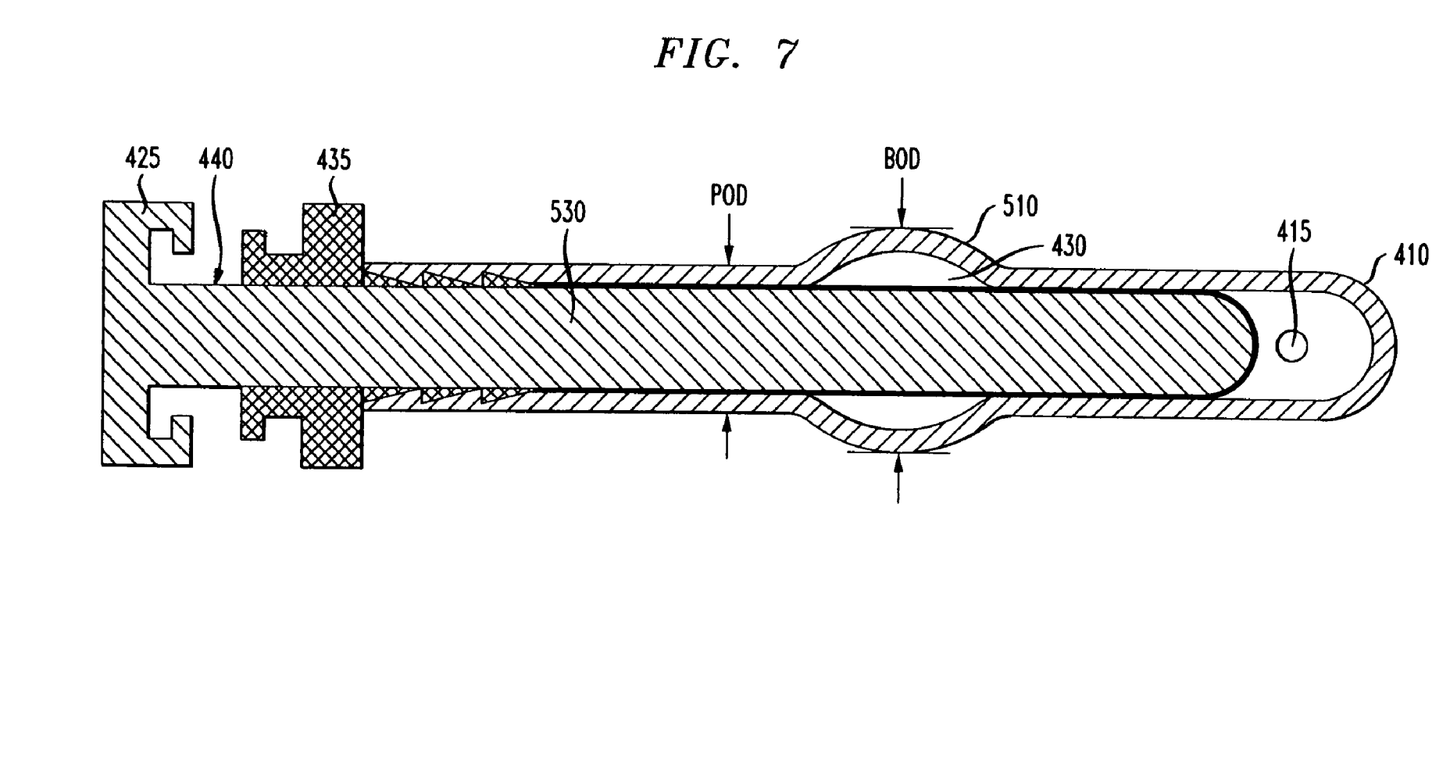
FIG. 7 depicts a cross-sectional view of the straight catheter of FIG. 5 with the pre-loaded stylet unlocked from the barb connector and the bulbous region of the catheter in a relaxed or non-stressed state having a maximum outer diameter greater than that of the non-bulbous region having a substantially uniform outer diameter.

FIGS. 5-7 illustrate an alternative embodiment of an exemplary straight or non-step catheter 400 including a bulbous region 510 having a maximum outer diameter (BOD) and a non-bulbous region having a substantially uniform outer diameter (POD). In contrast to the step catheter shown in FIGS. 1-4, the straight or non-step catheter 400 is formed from a single section thereby eliminating the step between the proximal and distal sections. The bulbous region 510 is made of an elastically deformable material with an elastic shape memory.

As shown in FIG. 5, the bulbous region 510 of the straight catheter 400 while in a relaxed or non-tensioned state has a maximum outer diameter (BOD) greater than that while in a stretched or stressed state. FIG. 6 depicts the exemplary straight catheter 400 with an assembled stylet 440 inserted and locked via connector 435 therein. The stylet 440 utilized with the straight catheter is designed differently than that previously described for the step catheter embodiment. Specifically, the stylet 440 for the straight catheter has a body 530 with a substantially uniform outer diameter thereby eliminating the shoulder 205 and reduced diameter arm 220. As illustrated in FIG. 6, the distal end of the stylet 440 is inserted in lumen 430 starting from the proximal end 405 and extending at least through the bulbous region 510, preferably in contact with the closed distal end 410 of the catheter 400 or some other physical impediment (e.g., rim, shoulder or projection) extending into the lumen 430. While in a stretched or stressed state, as shown in FIG. 6, bulbous region 510 has a reduced maximum outer diameter relative to that when in relaxed or non-stressed state, preferably, a substantially uniform outer diameter (POD) over the entire body of the catheter so it may be easily positioned at a targeted site. Once properly positioned, the stylet hub 425 is disengaged from the connector 435 and both removed from the catheter 400, so as to allow the bulbous region 510 to retract axially and return to its enlarged non-uniform outer diameter (BOD) relative to the non-bulbous region having a substantially uniform outer diameter (POD) thereby reducing or substantially preventing back flow. The straight catheter 400 may be designed to include any number of one or more ports 415 disposed, as desired, proximate the distal end of the catheter.

The first embodiment heretofore described with reference to FIGS. 1-7 represents a configuration in which (i) when in a relaxed or non-stressed state the maximum outer diameter of the bulbous region is greater than that of the substantially uniform outer diameter of the non-bulbous region of the proximal section so that the outer diameter over the entire proximal section is non-uniform; and (ii) when in a stretched or stressed state the maximum outer diameter of the bulbous region is reduced relative to when in a relaxed or non-stressed state and, preferably, the maximum outer diameter over the entire proximal section is substantially uniform when the bulbous region is in a stretched or stressed state. An alternative embodiment is shown in FIGS. 8-13 in which (i) when in a relaxed or non-stressed state the maximum outer diameter of the bulbous region is reduced relative to when in a stressed state and, preferably, the maximum outer diameter over the entire proximal section is substantially uniform when in a relaxed or non-stressed state; and (ii) when in a stressed state the maximum outer diameter of the bulbous region is greater than that of the substantially uniform outer diameter of the non-bulbous region of the proximal section while in a relaxed or non-stressed state so that the outer diameter over the entire proximal section is non-uniform.

Figure 8:
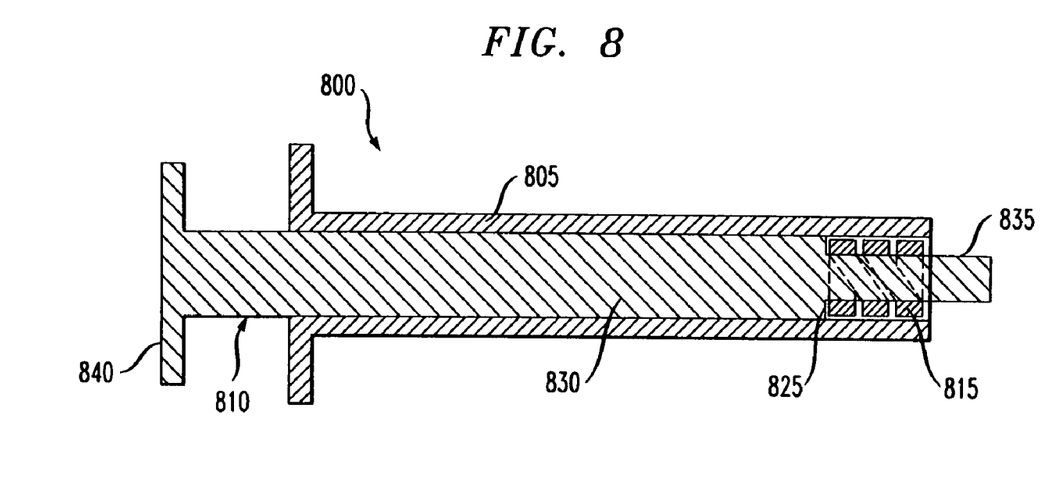
FIG. 8 represents a cross-sectional view of an exemplary stylet with a pre-loaded deployment member therein in accordance with a second embodiment of the present invention.
Figure 12:
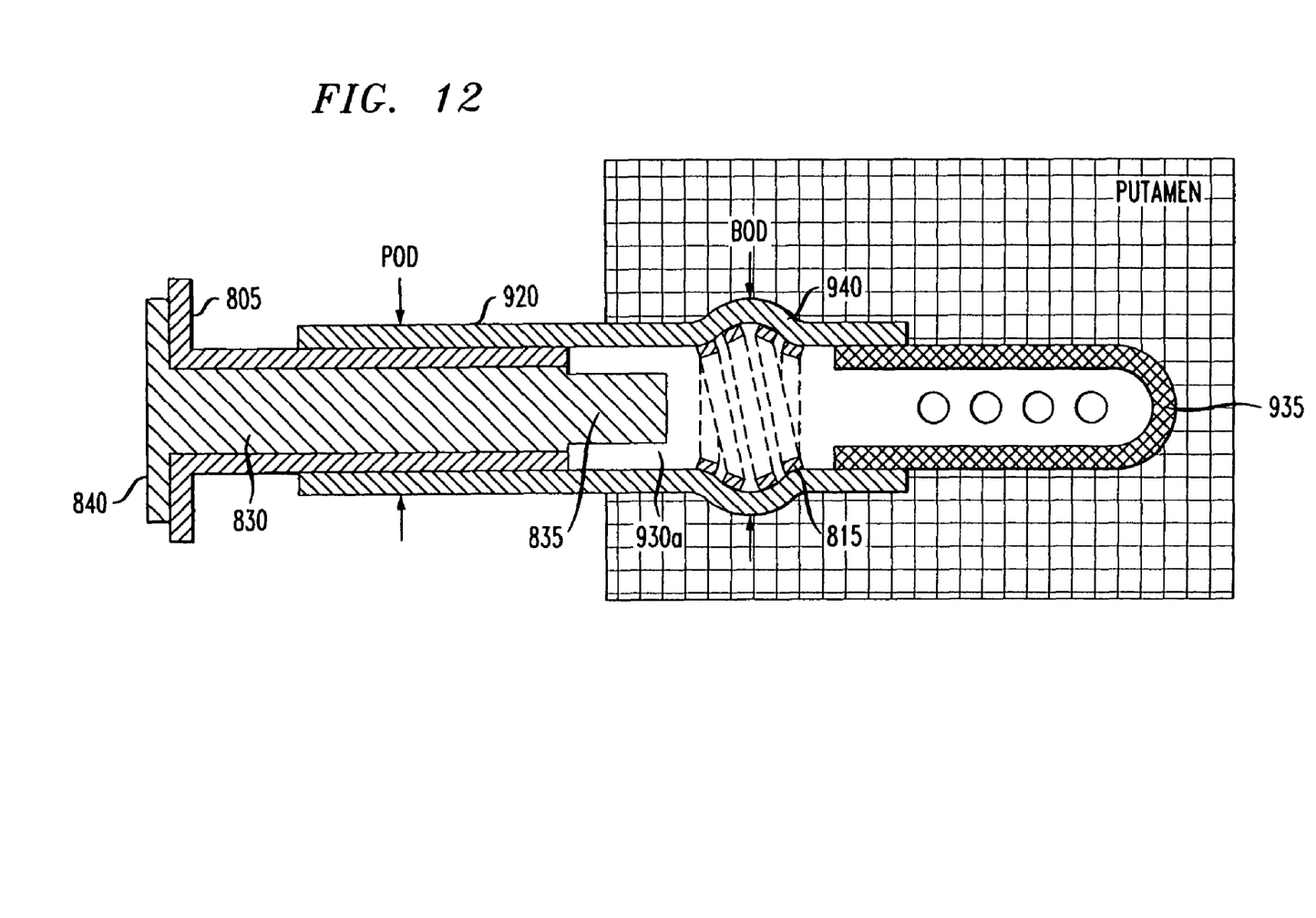
FIG. 12 diagrammatically depicts removal of the stylet leaving in place the fully actuated deployment member to form a bulbous region having an enlarged outer diameter in the proximal section of the step catheter.
Figure 13:
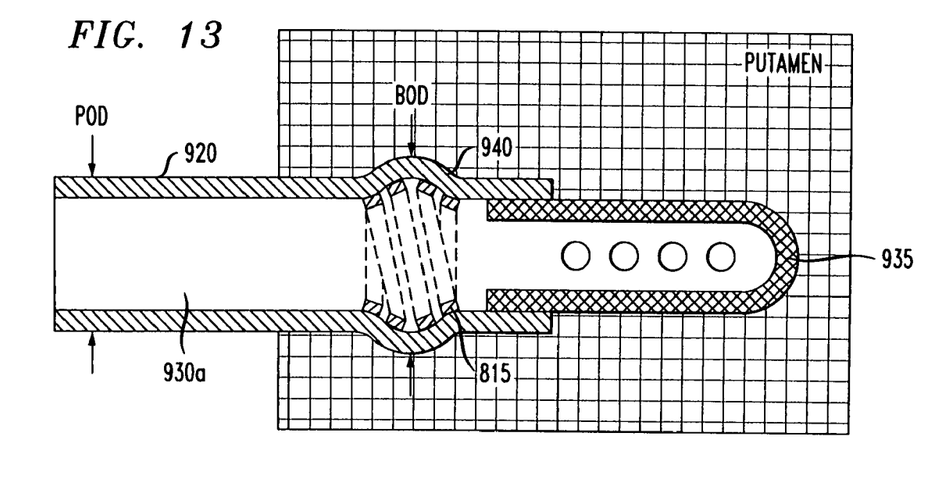
FIG. 13 represents the step catheter implanted at the targeted site after removal of the stylet wherein the proximal section of the catheter is maintained in a stressed state having a non-uniform outer diameter due to bulbous region formed as a result of the force imposed by the actuated deployment member.

FIG. 8 represents a stylet 800 including a pre-loaded tensioned deployment member 815 therein. Stylet 800 includes an outer body member 805 and an inner body member or plunger 810 disposed telescopically therein so as to be axially displaceable relative to the outer body member. The proximal end of the inner body member 810 terminates with a hub 840. At its opposite distal end, the inner body member 810 has a shoulder 825 followed by an arm 835 of reduced diameter, as shown in FIG. 12. Deployment member 815 is disposed between the outer body member 805 and the arm 835. In a preferred embodiment, when the inner body member 810 is fully inserted in the outer body member 805, the outer body member 805 overlaps or passes axially over the deployment member 815. While in this position, the deployment member 815 is bounded radially between the arm 835 of the inner body member 810 and the outer body member 805. Deployment member 815 is maintained in a compressed state when pre-loaded into the stylet due to the friction force with the outer body member 805. The outer and inner body members 805, 810 while in this position may be locked axially in position relative to one another via any conventional releasable connector such as that shown in FIGS. 1-7 to insure that the deployment member 815 is not unintentionally actuated during implantation and positioning of the catheter. Deployment member 815 may be any device or mechanism that compresses/expands radially. For instance, deployment member 815 may be a spring or coil (e.g., a NiTi coil). The proximal surface of the deployment member 815 is supported by shoulder 825.

Figure 9:
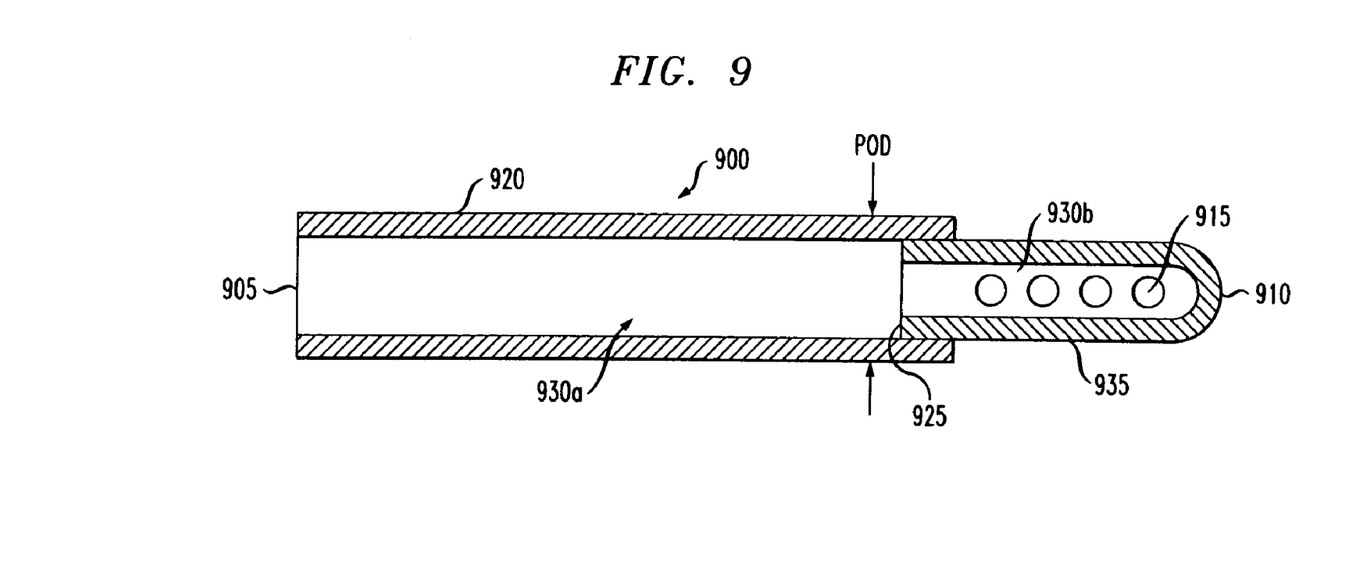
FIG. 9 represents a cross-sectional view of an exemplary step catheter in accordance with the second embodiment of the present invention.

A catheter 900 in accordance with this alternative embodiment is shown in FIG. 9 and may be manufactured using those same materials described above with respect to the embodiment shown in FIGS. 1-7. The catheter 900 is fabricated so that (i) when in a relaxed or non-stressed state the maximum outer diameter of the bulbous region is reduced relative to when in a stressed state and, preferably, the maximum outer diameter over the entire proximal section is substantially uniform when in a relaxed or non-stressed state; and (ii) when in a stressed state the maximum outer diameter of the bulbous region is greater than that of the substantially uniform outer diameter of the non-bulbous region of the proximal section while in a relaxed or non-stressed state so that the outer diameter over the entire proximal section is non-uniform.

Figure 10:
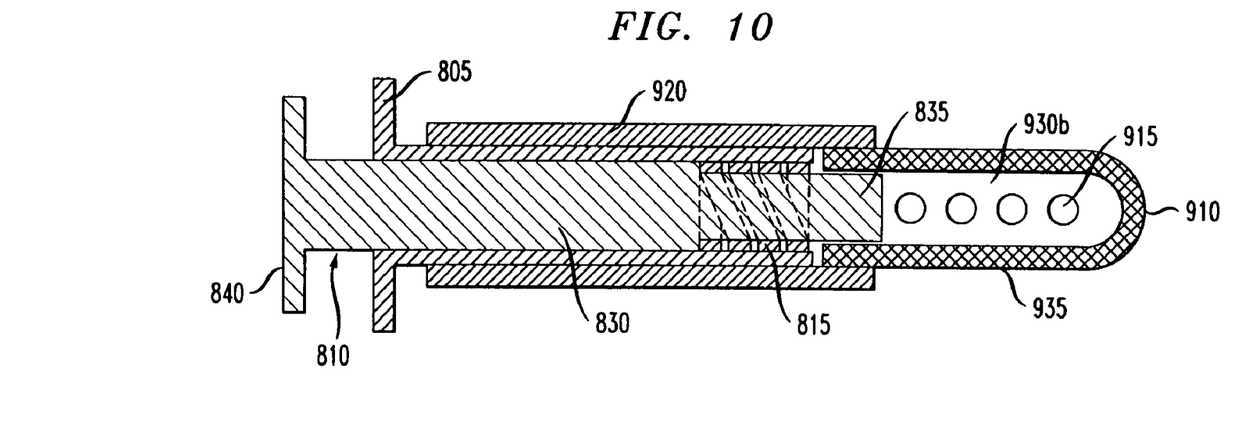
FIG. 10 shows a cross-sectional view of the assembled stylet and step catheter of FIGS. 8 and 9 with the catheter in a relaxed or non-stressed state.
Figure 11:
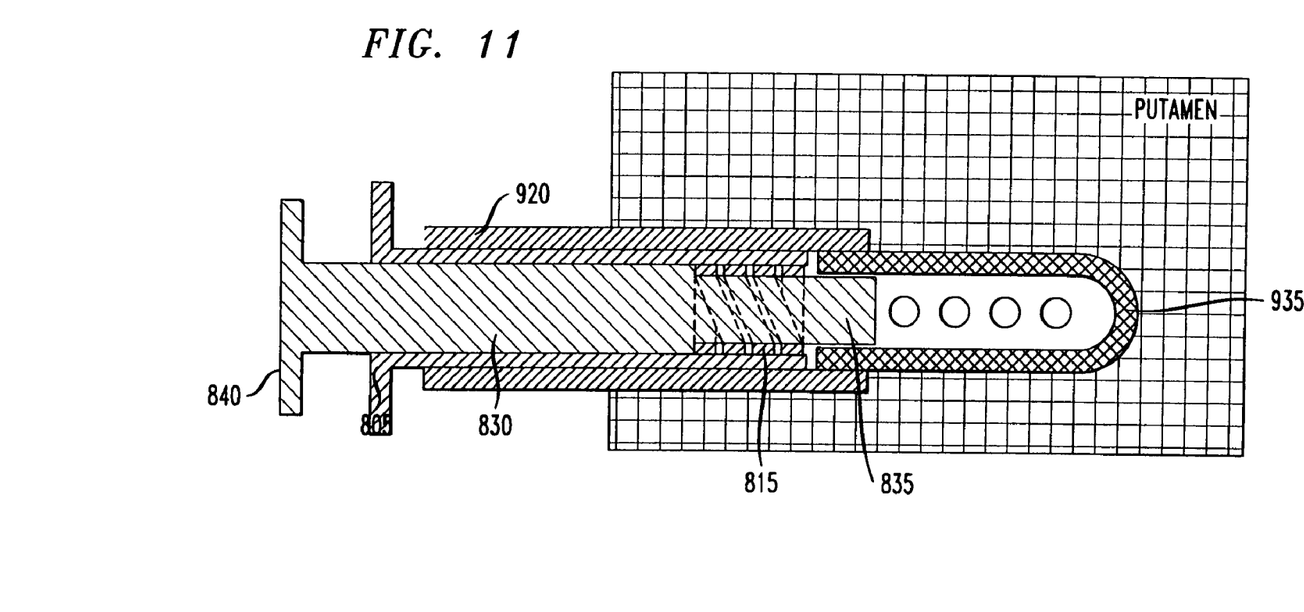
FIG. 11 depicts a cross-sectional view of the assembly of FIG. 10 positioned at the targeted site with the deployment member partially actuated and the catheter in a stressed state.

The stylet 800 with the pre-loaded deployment member 815, preferably while locked in position relative to one another, are inserted into the lumen 930a via the proximal section 920 of the catheter 900. Referring to FIG. 10, pre-loaded stylet 800 is preferably inserted so that at least a portion of the arm 835 of the inner body member 810 extends into the lumen 930b of the distal section 935 of the catheter 900 to provide strength and rigidity during insertion. So long as the deployment member 815 has not been actuated, the proximal section 920 of catheter 900 with the stylet 800 disposed therein will have a substantially uniform outer diameter so that it may be positioned at any desired targeted site. Once properly positioned at the targeted site, the outer body member 805 is axially displaced relative to the deployment member 815 and inner body member 810 in a direction toward the hub 840, as shown in FIG. 11. Outer body member 805 is axially displaced in FIG. 12 sufficiently to clear the deployment member 815 allowing it to fully actuate, release or activate.

When actuated, released or activated deployment member 815 expands radially imposing a force or stress on the proximal section 920 of the catheter causing its outer diameter to enlarge thereby forming the bulbous region 940. The direction (e.g. radial, axial) of the force may be varied, as desired, so long as the proximal section 920 when subject to that force exhibits a non-uniform outer diameter due to the bulbous region 940. Thereafter, in FIG. 13 the outer and inner body members 805, 810 are removed. Catheter 900 remains positioned at the targeted site with the deployment member 815 forming an enlarged diameter bulbous region 940 in its proximal section 920 that reduces or substantially prevents back flow of infusate along the catheter track.

A step down catheter configuration is shown in FIGS. 8-13, but the present invention may also be used with other designs such as a straight catheter. In addition, more than one bulbous region may be formed in the proximal section 920. Moreover, the number of openings 915 in the distal section 935 of the catheter may be changed or eliminated altogether, as desired. Catheter 900 has an open distal end 910, but may instead be closed off permitting passage exclusively through one or more openings 915.

The use of a stylet or guidewire disposed within the lumen of the catheters in accordance with the present invention eliminates the need for a permanently affixed delivery sheath that would disadvantageously enlarge the opening around the outer diameter of the distal end of the catheter and thereby create a larger allowance prone to reflux, back flow or leakage.

Catheters in accordance with the present invention are suitable for use with the delivery of a therapeutic agent or fluid directly into a targeted tissue. One example of such application is for the treatment of brain cancer or Parkinson's disease, wherein the delivery of infusate is directly to the grey matter tissue or specifically the putamen. Some additional possible uses may be found in the treatment of obesity, depression, stroke, epilepsy, or other movement disorders. Other alternative uses may include the targeted treatment of tumors elsewhere in the body such as the liver or spinal cord, the delivery of angiogenic factors to sick or dying deep tissue, such as in muscle, the delivery of nutrients or growth factors to places where capillary damage has prevented adequate delivery of nutrients or healing factors. Still other alternative uses are contemplated and within the intended scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A therapeutic agent delivery system comprising:
    a catheter having a proximal end and an opposite distal end, the catheter having a body with a lumen defined therein; the body including a non-bulbous region having a substantially uniform outer diameter and a radially closed bulbous region, the bulbous region being made from an elastically deformable material; while in a first state the bulbous region having a maximum outer diameter greater than the substantially uniform outer diameter of the non-bulbous region; and while in a second state the maximum outer diameter of the bulbous region being reduced relative to that while in the first state; wherein the bulbous region of the body of the catheter is adapted to transition between the first and second states prior to introduction of a therapeutic agent via the lumen, wherein the first state in a non-stressed state and the second state is a stressed state, wherein the maximum outer diameter of the bulbous region while in the second state is substantially equal to the substantially uniform outer diameter of the non-bulbous region.

2. The system in accordance with claim 1, wherein the bulbous region is disposed proximate the distal end of the catheter.

3. The system in accordance with claim 1, wherein the body of the catheter further comprises:
    a proximal section disposed closest to the proximal end of the catheter; and
    a distal section disposed closest to the distal end of the catheter, the lumen extending through both the proximal and distal sections; the bulbous and non-bulbous regions being defined in the proximal section.

4. The system in accordance with claim 3, wherein the proximal section is formed of an elastically deformable material; and the distal section is formed of a substantially rigid material.

5. The system in accordance with claim 3, further comprising a stylet configured to be received in the lumen starting from the proximal end of the catheter and extending into at least a portion of the distal section.

6. The system in accordance with claim 5, wherein a distal end of the stylet extends into the at least the portion of the distal section that overlaps with the proximal section.

7. The system in accordance with claim 5, further comprising a connector for releasably securing the stylet inserted in the catheter while the bulbous region is in the first state.

8. The system in accordance with claim 1, further comprising a stylet configured to be received in the lumen starting from the proximal end of the catheter and extending at least through the bulbous region.

9. The system in accordance with claim 8, further comprising a connector for releasably securing the stylet inserted in the catheter while the bulbous region is in the first state.

10. The system in accordance with claim 3, further comprising:
    a stylet that includes an outer body member axially displaceable relative to an inner body member; the inner body member having a hub, a first section of substantially uniform outer diameter, a shoulder, and an arm smaller in diameter relative to that of the first section; and
    a deployment member disposed between the outer body member and the arm of the inner body member; and the lumen is configured to permit passage of the inner and outer body members of the stylet therein starting from the proximal end of the catheter, the shoulder contacts the proximal end of the distal section with the arm extending into at least a portion of the lumen disposed in the distal section.

11. A method for using a therapeutic agent delivery system, the delivery system includes a catheter having a proximal end and an opposite distal end; the catheter having a body with a lumen defined therein, the body including a non-bulbous region having a substantially uniform outer diameter and a radially closed bulbous region, the bulbous region being made from an elastically deformable material, comprising the steps of:
    inserting a stylet into the lumen starting at the proximal end of the catheter and extending through at least the bulbous region;

implanting the assembled stylet and catheter in a patient at a targeted site while the bulbous region is in a first state in which the maximum outer diameter of the bulbous region is substantially equal to the substantially uniform outer diameter of the non-bulbous region; and removing the assembled stylet from the catheter while the bulbous region of the catheter is maintained in a second state in which the maximum outer diameter of the bulbous region is greater than in the first state so as to reduce back flow;

wherein the first state is a non-stressed state and the second state is a stressed state.

12. The method in accordance with claim 11, wherein prior to the removing step, further comprising the step of applying a radial force to the catheter so that the bulbous region is in a stressed state in which its maximum outer diameter is enlarged relative to that while in a non-stressed state.

13. The method in accordance with claim 11, wherein the body of the catheter comprises:
   a proximal section disposed closest to the proximal end of the catheter; and
   a distal section disposed closest to the distal end of the catheter, the lumen extending through both the proximal and distal sections; the bulbous and non-bulbous regions being defined in the proximal section.

14. The method in accordance with claim 13, wherein the proximal section is formed of an elastically deformable material; and the distal section is formed of a substantially rigid material.

15. The method in accordance with claim 13, wherein the stylet includes an outer body member axially displaceable relative to an inner body member; the inner body member having a hub, a first section of substantially uniform outer diameter, a shoulder, and an arm smaller in diameter relative to that of the first section; and the lumen of the catheter has located therein a deployment member disposed between the outer body member and the arm of the inner body member; and the lumen is configured to permit passage of the inner and outer body members of the stylet therein starting from the proximal end of the catheter, the shoulder contacts the proximal end of the distal section with the arm extending into at least a portion of the lumen disposed in the distal section.

16. The method in accordance with claim 11, further comprising the step of dispensing a therapeutic agent while the bulbous region is in the second state applying outward radial pressure against surrounding tissue circumferentially about the catheter creating a barrier that substantially prevents reflux of the therapeutic agent exterior of the catheter.

17. The system in accordance with claim 1, wherein the bulbous region while in the first state creates a barrier that substantially prevents reflux exterior of the catheter.

18. The method in accordance with claim 11, wherein the bulbous region of the body of the catheter is adapted to transition between the first and second states prior to introduction of a therapeutic agent via the lumen.

19. The system in accordance with claim 5, wherein the stylet is removable from the catheter.

* * * * *